(12) United States Patent
Pryor

(10) Patent No.: US 7,473,272 B2
(45) Date of Patent: Jan. 6, 2009

(54) RECAPTURABLE STENT WITH MINIMUM CROSSING PROFILE

(75) Inventor: Jack Pryor, San Diego, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 264 days.

(21) Appl. No.: 11/207,170

(22) Filed: Aug. 17, 2005

(65) Prior Publication Data

US 2007/0043424 A1 Feb. 22, 2007

(51) Int. Cl.
- A61F 11/00 (2006.01)
- A61F 2/06 (2006.01)
- A61F 2/84 (2006.01)
- A61F 2/90 (2006.01)

(52) U.S. Cl. ......................... 623/1.12; 606/108; 623/1.2

(58) Field of Classification Search .................. 623/1.2, 623/1.12, 1.16, 1.3
See application file for complete search history.

(56) References Cited

U.S. PATENT DOCUMENTS

| | | | |
|---|---|---|---|
| 6,179,878 B1 * | 1/2001 | Duerig et al. | 128/898 |
| 7,056,328 B2 * | 6/2006 | Arnott | 606/200 |
| 2001/0029397 A1 | 10/2001 | Thompson | |
| 2002/0049490 A1 * | 4/2002 | Pollock et al. | 623/1.15 |

FOREIGN PATENT DOCUMENTS

| | | |
|---|---|---|
| EP | 0799607 | 10/1997 |
| EP | 1477136 | 11/2004 |
| WO | WO96/39077 | 12/1996 |
| WO | WO03/022172 | 3/2003 |

* cited by examiner

*Primary Examiner*—Thomas J Sweet
*Assistant Examiner*—Jonathan R Stroud
(74) *Attorney, Agent, or Firm*—Serge Hodgson

(57) ABSTRACT

A self-expanding stent includes a plurality of segments having an alternating repeating pattern; each of the segments having connected crowns and unconnected crowns, wherein the unconnected crowns can be fully straightened without damage or permanent distortion to the unconnected crowns; and connectors extending between and connecting adjacent connected crowns of adjacent segments. The self-expanding stent catheter has a minimum crossing profile and the stent compressed for deployment therein is recapturable.

14 Claims, 5 Drawing Sheets

US 7,473,272 B2

RECAPTURABLE STENT WITH MINIMUM CROSSING PROFILE

BACKGROUND OF THE INVENTION

1. Field of the Invention

The present invention relates to an intra-luminal device and method. More particularly, the present invention relates to a stent for treatment of intra-luminal diseases in human bodies.

2. Description of the Related Art

In stent deployment systems, a self-expanding stent is restrained within a sheath. After positioning the stent at the desired location via fluoroscopic guidance, the physician retracts the sheath to deploy the stent, i.e., to expose the stent and allow it to self-expand.

One factor important to maximize the range of anatomical variation in which the stent can be used, is the catheter crossing profile, i.e., more tightly compressible stent can be compressed to a smaller diameter when restrained within the sheath. More particularly, by minimizing the compressed diameter of the stent, the catheter including the stent can be made very small allowing the catheter to be inserted into and across very small openings and vessels.

SUMMARY OF THE INVENTION

In accordance with one embodiment, a self-expanding stent includes a plurality of segments having an alternating repeating pattern; each of the segments having connected crowns and unconnected crowns, wherein the unconnected crowns include smooth curves (or large radius) such that the unconnected crowns can be fully straightened without damage or permanent distortion to the unconnected crowns; and connectors extending between and connecting adjacent connected crowns of adjacent segments.

In accordance with another embodiment, a method includes stretching the self-expanding stent along a longitudinal axis of the self-expanding stent, the stretching including straightening the unconnected crowns. By straightening the unconnected crowns, the straightened stent has a minimum crossing profile. Further, once straightened, the stent has an absence of loose ends or other protrusions which can catch on a sheath being advanced over the stent. Accordingly, the stent is recapturable.

Embodiments in accordance with the present invention are best understood by reference to the following detailed description when read in conjunction with the accompanying drawings.

BRIEF DESCRIPTION OF THE DRAWINGS

Common reference numerals are used throughout the drawings and detailed description to indicate like elements.

DETAILED DESCRIPTION

Figure 1:
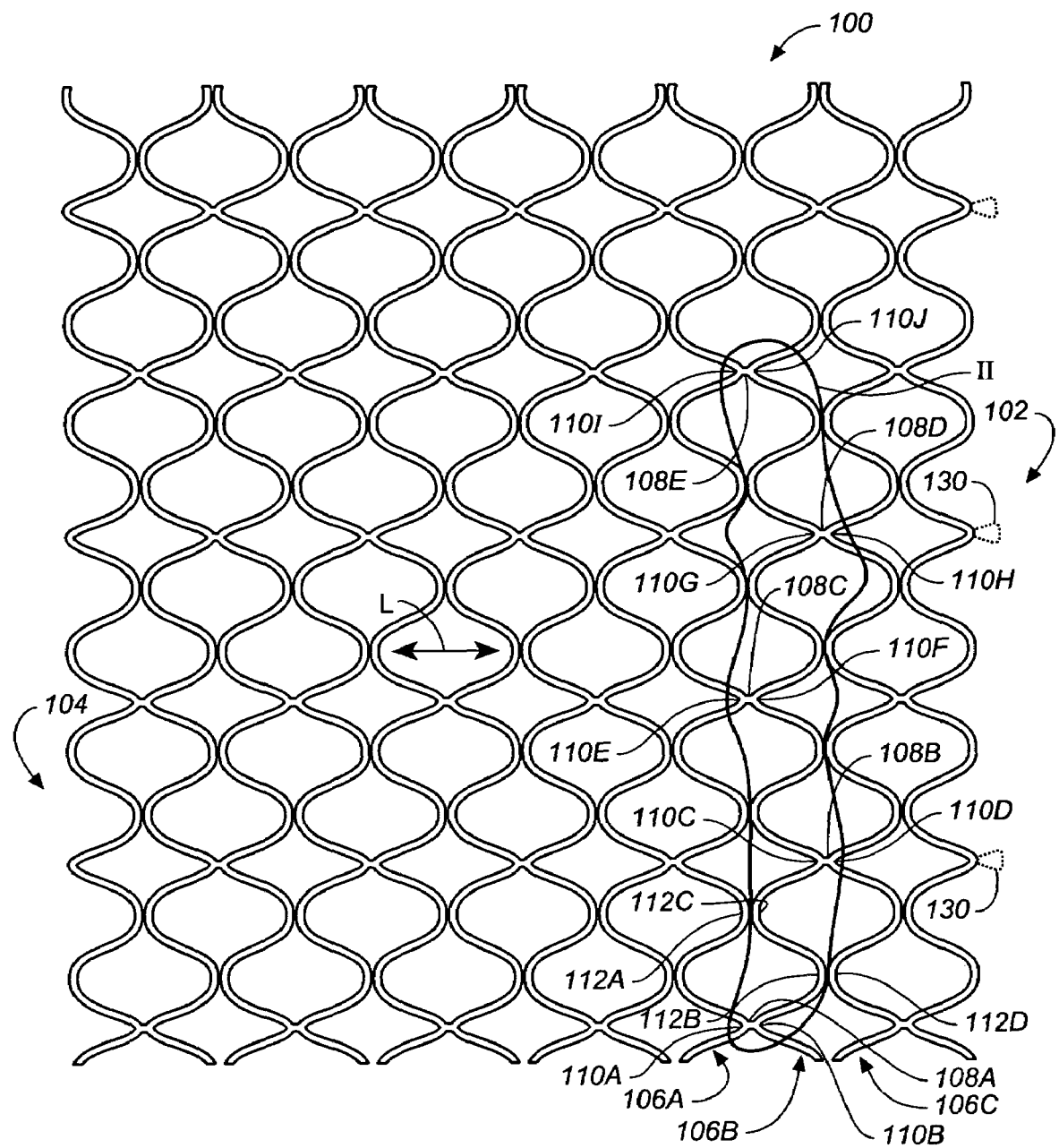
FIG. 1 is a plan view of a laid flat expanded stent in one embodiment according to the present invention.

In accordance with one embodiment, referring to FIG. 1, a self-expanding stent 100 includes a plurality of segments such as segments 106A, 106B, 106C having an alternating repeating pattern; each of the segments having connected crowns such as connected crowns 110B, 110C and unconnected crowns such as unconnected crowns 112B, 112C, wherein the unconnected crowns include smooth curves (or large radius) such that the unconnected crowns can be fully straightened without damage or substantially permanent distortion to the unconnected crowns; and connectors such as connectors 108A, 108B extending between and connecting adjacent connected crowns of adjacent segments.

Figure 2:
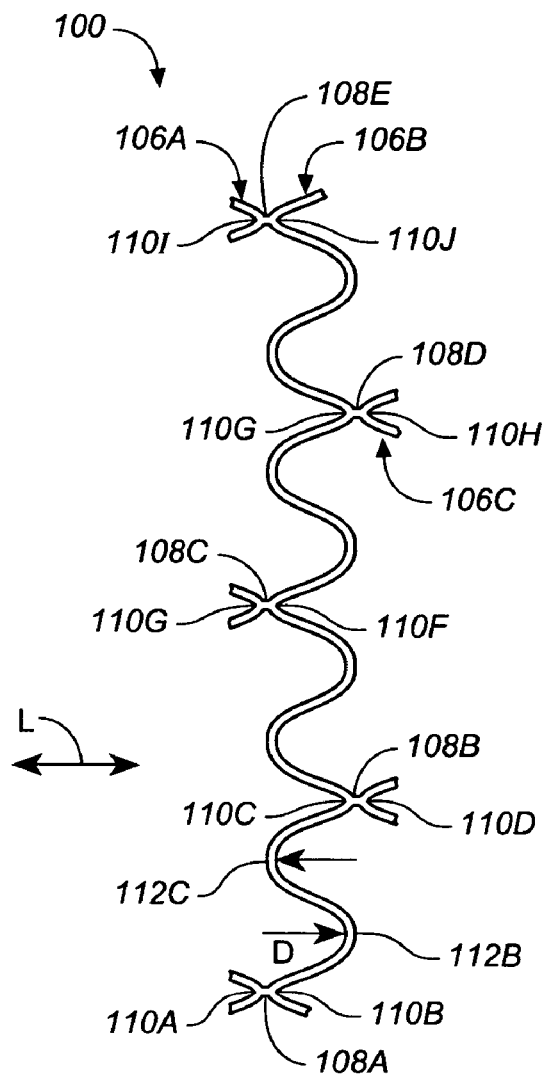
FIG. 2 is an enlarged plan view of a section II of the stent of FIG. 1.
Figure 3:
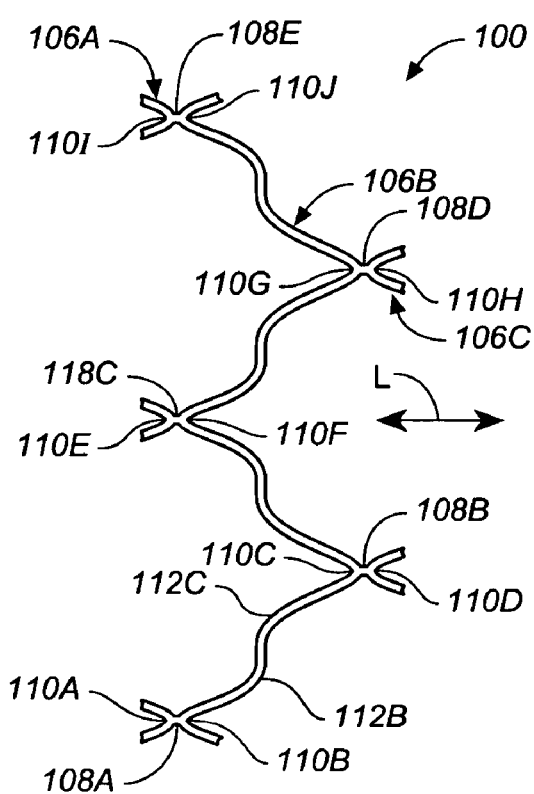
FIG. 3 is the enlarged plan view of the section II of the stent of FIG. 2 as the stent is pulled straight.
Figure 4:
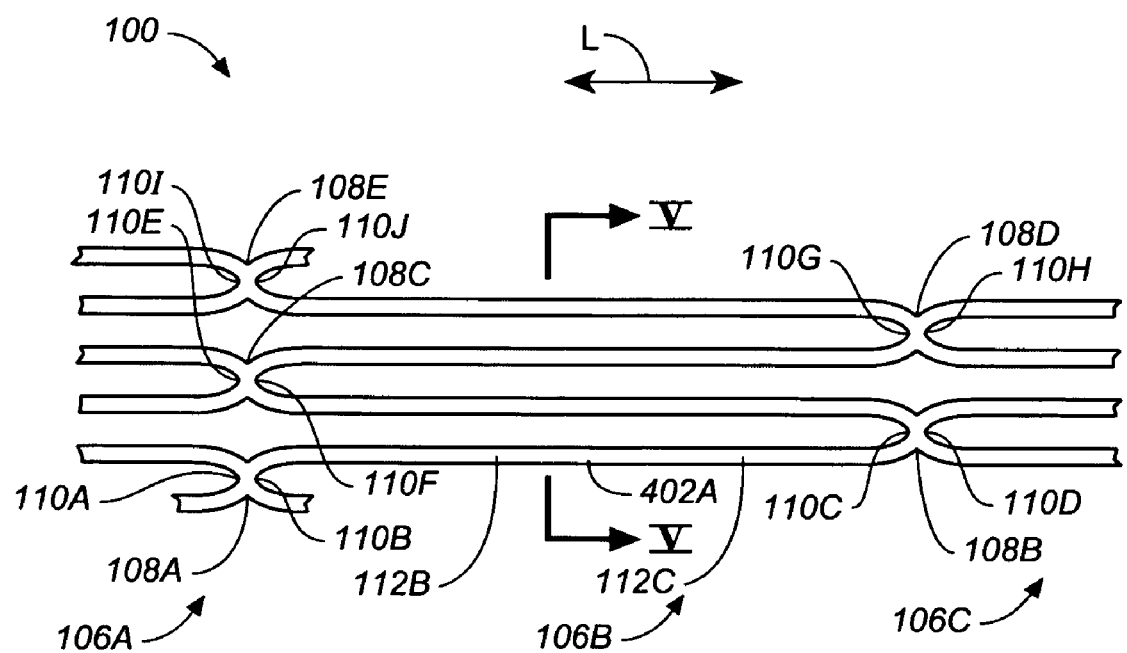
FIG. 4 is the enlarged plan view of the section II of the stent of FIG. 3 when the stent is fully elongated, sometimes called completely pulled straight.
Figure 7:
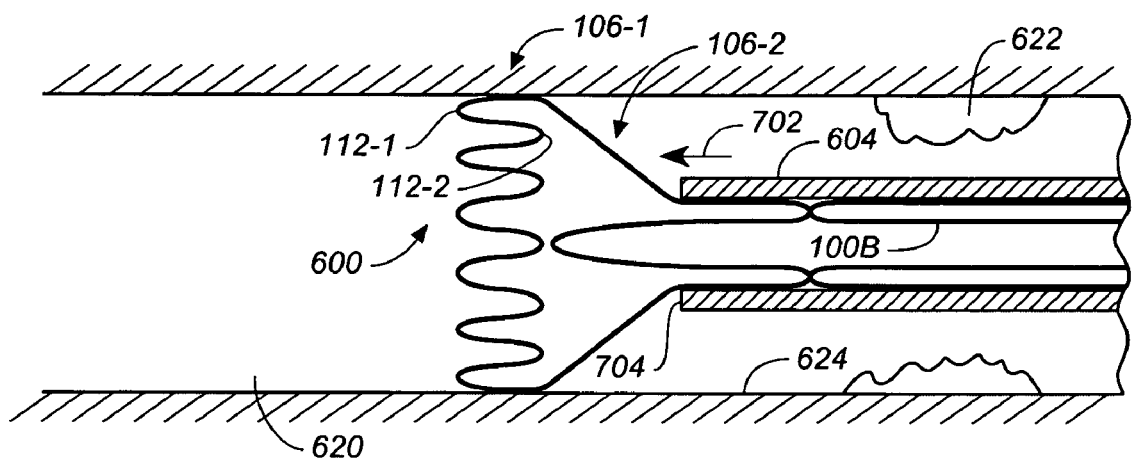
FIG. 7 is a modified partial cross-section view of the stent delivery system of FIG. 6 during deployment of the stent.

In accordance with another embodiment, referring to FIGS. 2, 3 and 4 together, a method includes stretching self-expanding stent 100 along a longitudinal axis L of self-expanding stent 100, the stretching including straightening the unconnected crowns such as straightening unconnected crowns 112B, 112C. By straightening the unconnected crowns, the straightened stent has a minimum crossing profile. Further, by pulling the proximal end of the stent back into the outer sheath, as with anchors well-known by someone skilled in the art, as the unconnected crowns catch on the outer sheath they are forced to straighten, thus allowing them to fit within the sheath as shown in FIG. 7. Accordingly, the stent is recapturable.

More particularly, FIG. 1 is a plan view of a laid flat expanded stent 100 in one embodiment according to the present invention. Stent 100 is cylindrical, having a longitudinal axis L. Stent 100 includes a distal, e.g., first, end 102 and a proximal, e.g., second, end 104.

Illustratively, stent 100 is integral, i.e., is a single piece and not a plurality of separate pieces connected together. For example, stent 100 is formed by laser cutting a tubular piece of material. However, stent 100 can also be formed of separate pieces, which are connected together, e.g., by welding.

Stent 100 is formed from a plurality of segments such as segments 106A, 106B, 106C. Each segment has a pattern, and this pattern is sometimes called serpentine or an alternating repeating pattern. Segments are coupled to one another at connectors such as connectors 108A, 108B, 108C, 108D, 108E. Connectors extend between connected crowns such as connected crowns 110A, 110B, 110C, 110D, 110E, 110F, 110G, 110H, 110I, 110J, sometimes called peaks and valleys or minima and maxima, of the alternating repeating patterns of the segments. Specifically, connected crowns of each segment are directly connected to the adjacent connected crowns of the adjacent segment of stent 100 by the connectors.

To illustrate, segment 106A includes three connected crowns 110A, 110E, 110I on one side. Segment 106B includes connected crowns 110B, 110C, 110F, 110G, 110J. Segment 106C includes connected crowns 110D, 110H.

Connectors 108A, 108B, 108C, 108D, 108E extend between and couple connected crowns 110A, 110B, connected crowns 110C, 110D, connected crowns 110E, 110F, connected crowns 110G, 110H, connected crowns 110I, 110J, respectively. The other connected crowns of the segments are connected to one another in a similar manner.

Further, the segments further include unconnected crowns that are adjacent to but unconnected to one another. To illustrate, segment 106A includes an unconnected crown 112A. Segment 106B includes unconnected crowns 112B, 112C. Segment 106C includes an unconnected crown 112D.

Unconnected crowns 112A and 112C are directly adjacent one another but are unconnected. Similarly, unconnected crowns 112B and 112D are directly adjacent one another but are unconnected.

In accordance with the example illustrated in FIG. 1, in each segment, there are two unconnected crowns between connected crowns. To illustrate, for segment 106B, unconnected crowns 112B and 112C are between connected crowns 110B and 110C. Although segments of stent 100 includes two unconnected crowns between connected crowns, in other examples, segments include more or less than two unconnected crowns between connected crowns.

FIG. 2 is an enlarged plan view of a section II of stent 100 of FIG. 1. Referring now to FIG. 2, unconnected crowns have an absence of sharp bends (which can equate to low strain levels as maximum strain is a function of bend radius and crown width). (There are equations for this, but they're only approximations for nitinol since it's nonlinear. An estimate based on a linear material says that strain equals crown width divided by bend diameter (2×radius). So if nitinol's maximum is 8%, the ratio of crown width to bend radius should be about 0.16, or: Width/Radius<0.16.) More particularly, unconnected crowns such as unconnected crowns 112B, 112C are smooth curves (or large radius) having an absence of a bend with an angle less than. In one example, unconnected crowns have a diameter D of 0.007 inches (0.178 mm) or greater.

As discussed in greater detail below with reference to FIGS. 3 and 4, by forming unconnected crowns as smooth curves (or larger radius), unconnected crowns can be pulled straight without damage or permanent distortion to unconnected crowns.

FIG. 3 is the enlarged plan view of section II of stent 100 of FIG. 2 as stent 100 is partially pulled straight. Referring now to FIGS. 1 and 3 together, stent 100 is stretched along longitudinal axis L. More particularly, distal end 102 is moved relatively away from proximal end 104 such that the distance along longitudinal axis L between distal end 102 and proximal end 104 increases.

As a result, referring now to FIG. 3, the distance along longitudinal axis L between connected crowns of each segment increases. To illustrate, the distance along longitudinal axis L between connected crowns 110C, 110G and connected crowns 110B, 110F, 110J of segment 106B increases. This causes unconnected crowns of each segment to become straightened, i.e., to extend into a straight or nearly straight position or form. As used herein, to be straight includes lying at full length and spread out with substantially less curvature than when relaxed. By forming unconnected crowns as smooth curves (or large radius), unconnected crowns can readily be pulled straight, sometimes called pulled flat, without damage or permanent distortion of unconnected crowns.

FIG. 4 is the enlarged plan view of section II of stent 100 of FIG. 3 when stent 100 is fully elongated, sometimes called completely pulled straight. Referring now to FIG. 4, stent 100 is fully stretched along longitudinal axis L.

As a result, the distance along longitudinal axis L between connected crowns is at a maximum. To illustrate, the distance along longitudinal axis L between connected crowns 110C, 110G and connected crowns 110B, 110F, 110J of segment 106B is the maximum possible distance. Any further stretching of stent 100 would damage and permanently distort stent 100.

Further, unconnected crowns of each segment are straight. Accordingly, each segment includes straight sections between adjacent connected crowns of the segment. The straight sections are essentially parallel to longitudinal axis L of stent 100. Each of the straight sections includes two unconnected crowns that have been straightened.

To illustrate, unconnected crowns 112B, 112C of segment 106B are completely straight. Segment 106B includes straight sections including a straight section 402A between adjacent connected crowns 110B and 110C of segment 106B. Straight section 402A is essentially parallel to longitudinal axis L of stent 100. Straight section 402A includes two unconnected crowns 112B, 112C that have been straightened.

In one example, stent 100 is formed from a memory metal such as nickel titanium alloy, e.g., nitinol. When pulled straight (FIG. 4), the unconnected crowns of stent 100 are subjected to a maximum 8% strain, which is within the acceptable limit to avoid damage or permanent distortion of the unconnected crowns.

When completely pulled straight as illustrated FIG. 4, stent 100 has a minimum outside diameter which allows the catheter containing it to have a minimum crossing profile (or outside diameter (or minimum circumference when stent elements are close or tightly circumferentially packed which allows the catheter combining it to have a minimum crossing profile (or outside diameter))) as discussed further below in reference to FIG. 5. More particularly, instead of having a plurality of unconnected crowns radially collapsed in upon one another such as would be the case if the expanded stent 100 of FIG. 1 was radially compressed within a sheath without being pulled straight, by pulling stent 100 straight prior to radially compressing stent 100 within a sheath, only straight sections of stent 100 are collapsed in upon one another. Since there is only one straight section for every two unconnected crowns, the crossing profile of stent 100 is drastically reduced.

Figure 5:
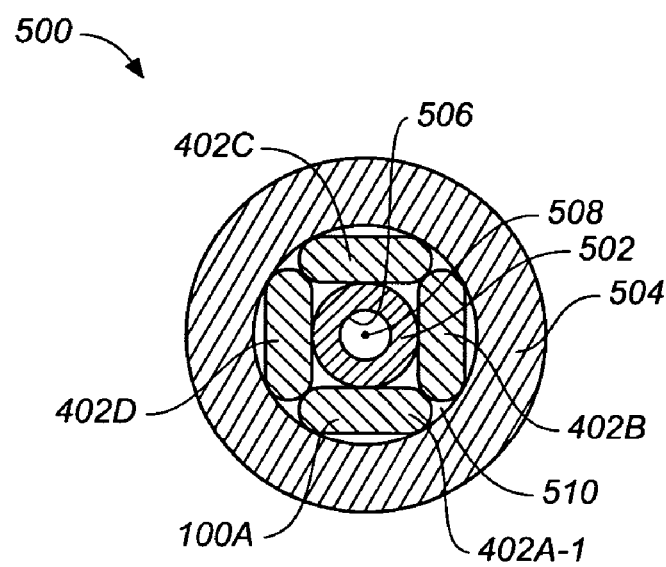
FIG. 5 is a cross-sectional view of a stent delivery system including a stent in one embodiment according to the present invention.

FIG. 5 is a cross-sectional view of a stent delivery system 500 including a stent 100A. Delivery system 500 includes an inner member 502, stent 100A, and a sheath 504. Although not illustrated, delivery system 500 includes other structures well known to those of skill in the art such as a handle.

In accordance with this embodiment, inner member 502, sometimes called a pushrod, is a hollow tubular member and includes a lumen 506, e.g., a guidewire lumen, through which a guidewire 508 extends.

Stent 100A is stretched flat, placed over and around inner member 502, and constrained by sheath 504. In one embodiment, inner member 502 and/or stent 100A include radiopaque markers, which allow the location of stent 100A to be precisely tracked facilitating positioning of stent 100A within a vessel. Sheath 504 includes a lumen 510 through which inner member 502 and guidewire 508 extend.

Stent 100A includes four straight sections 402A-1, 402B, 402C and 402D. Each of straight sections 402A-1, 402B, 402C and 402D are similar to straight section 402A of stent 100 of FIG. 4 and include two straightened unconnected crowns. For purposes of illustration, if the laid flat pattern illustrated in FIG. 4 was formed into a cylindrical stent such that crown 110B and crown 110J were in fact the same crown and a cross-sectional view of the cylindrical stent was taken along the line V-V in FIG. 4, a structure similar to stent 100A of FIG. 5 would be seen.

As shown, stent 100A has a minimal outside diameter. In one example, the diameter of guide wire 508 is the limiting factor in the outside diameter of delivery system 500. Specifically, the outside diameter does not depend on the total number of crowns of stent 100A. Rather, the outside diameter depends upon the number of connectors between segments (or in each segment) of stent 100A. Large diameter stents similar to stents 100, 100A but with more unconnected crowns between connected crowns may be formed without an increase in the outside diameter. Of course, when straightened, the length of the large diameter stents will be greater than the length of straightened stents 100, 100A.

Further, as shown in FIG. 4, when stent 100A is fully straightened, stent 100A has an absence of loose ends or other protrusions. Accordingly, in the event that the initial partial deployment of stent 100 is unsatisfactory, stent 100A can re-sheathed, sometimes called recaptured, simply by pulling stent 100A back into sheath 504.

Figure 6:
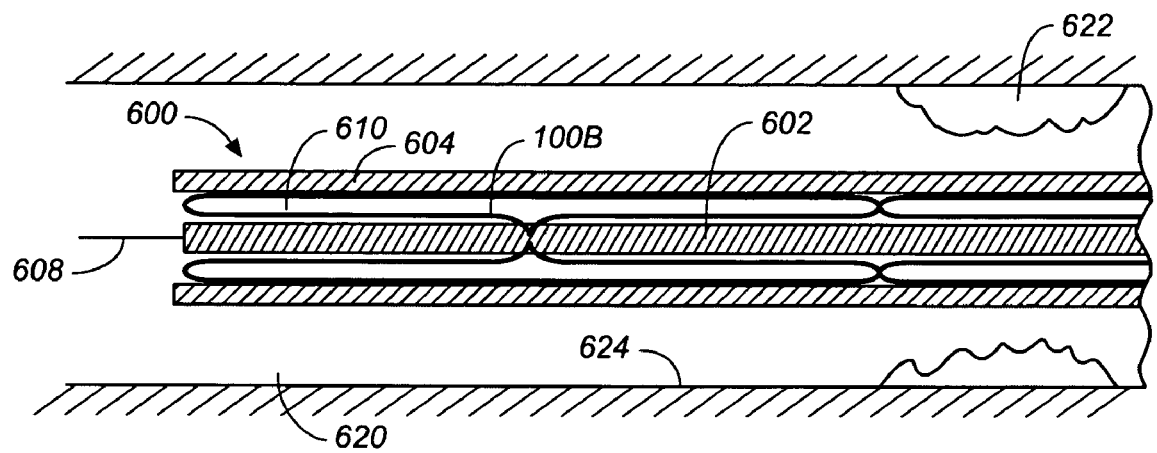
FIG. 6 is a modified partial cross-section view of a stent delivery system within a parent vessel of a patient adjacent to an occlusion.

FIG. 6 is a modified partial cross-section view of a stent delivery system 600 within a parent vessel 620 of a patient adjacent to an occlusion 622. Occlusion 622 occludes or completely blocks blood flow through parent vessel 620. Illustratively, occlusion 622 is plaque, thrombi, other deposits, emboli or other substances on an inner vessel wall 624 of parent vessel 620. Occlusion 622 reduces the blood carrying capacity of parent vessel 620. Left untreated, occlusion 622 could cause serious and permanent injury, or even death to the patient.

Delivery system 600 includes an inner member 602, a fully straightened stent 100B, and a sheath 604. Although not illustrated, delivery system 600 includes other structures well known to those of skill in the art such as a handle.

Inner member 602, sometimes called a pushrod, is a hollow tubular member and includes a lumen (not shown), e.g., a guidewire lumen, through which a guidewire 608 extends.

Fully straightened stent 100B is radially constrained by sheath 604. More particularly, prior to deployment, fully straightened stent 100B is located within sheath 604. Sheath 604 includes a lumen 610 through which inner member 602 and guidewire 608 extend.

Figure 8:
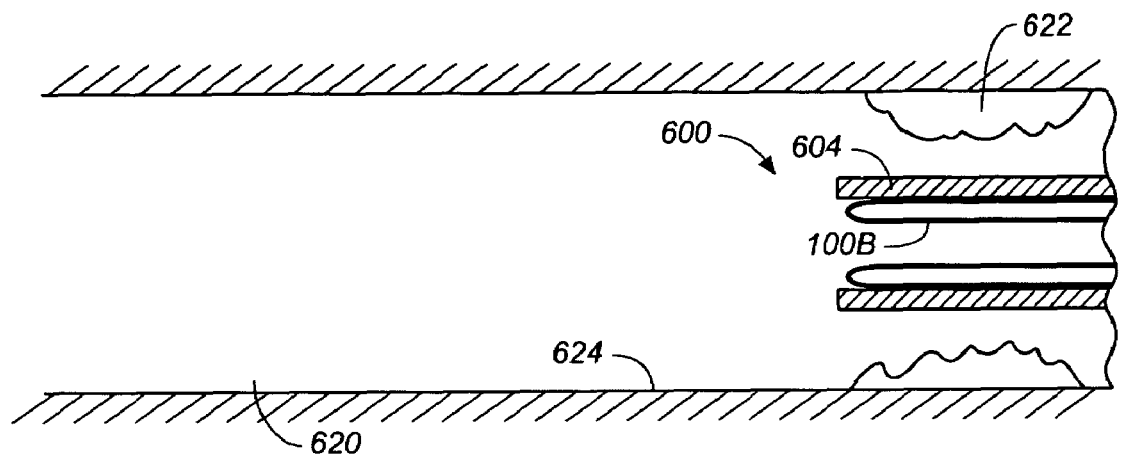
FIG. 8 is a modified partial cross-section view of the stent delivery system of FIG. 7, the stent having been recaptured from the partial deployment shown in FIG. 7.
Figure 9:
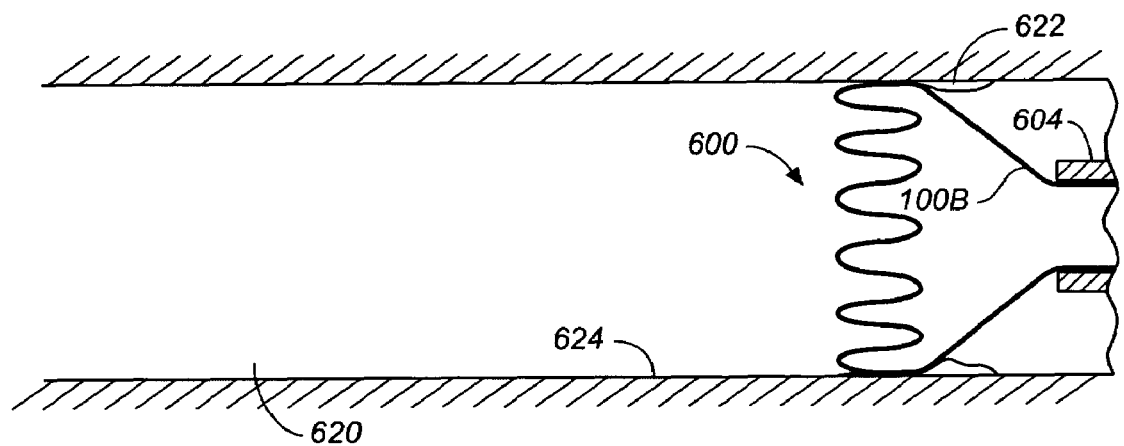
FIG. 9 is a modified partial cross-section view of the stent delivery system of FIG. 8 during re-deployment of the stent.

FIG. 7 is a modified partial cross-section view of stent delivery system 600 of FIG. 6 during deployment of stent 100B. In FIGS. 7, 8, and 9, inner member 602 and guidewire 608 are not illustrated for clarity of presentation.

Referring now to FIGS. 6 and 7 together, to deploy stent 100B, sheath 604 is retracted by the physician. As sheath 604 is retracted, the first few segments, e.g., segments 106-1, 106-2, of stent 100B, i.e., a portion of stent 100B, are uncovered by sheath 604 and exposed. As a result, the first few segments of stent 100B radially self-expand into inner vessel wall 624 of parent vessel 620. Further, the first few segments of stent 100B self-un-straighten, sometimes called self-curl. More particularly, unconnected crowns such as unconnected crowns 112-1, 112-2 of the deployed segments return to be smooth curves (or large radius). Generally, the straight sections of the deployed segments return to be curved as the unconnected crowns return to be smooth curves (or larger radius). Stent 100B is a self-expanding type stent, e.g., formed of a super elastic memory metal.

These first few segments of stent 100B are slowly and carefully deployed by the physician. This allows the physician to deploy the first few segments of stent 100B and assess the position of stent 100B within parent vessel 620 with respect to the location of occlusion 622. A necessary feature of a delivery system for this type of stent, unlike conventional stent delivery systems (catheters) which only require that the outer sheath be retracted, the inner member may need to be simultaneously advanced (moved opposite the outer sheath) because of the high amount of foreshortening. In a typical embodiment, this can be done automatically by a simple gear or lever mechanism in the handle. The action would be reversed to recapture the stent. For example, if the stent if 50 mm long unconstrained, but 150 mm long within the sheath, once the distal end is deployed and anchored in the vessel, the proximal end will need to move forward 100 mm to deploy correctly. So while the outer sheath moves proximally 50 mm, the inner member moves forward 100 mm, so that the stent is deployed correctly.

In the event that the positioning of stent 100B with respect to the location of the occlusion 622 is unsatisfactory, the physician can stop retraction of sheath 604 and forward motion of the center (inner) member. The physician can then reverse the direction of sheath 604 and inner member, so that the sheath 604 moves relative to the inner member and stent 100B to recapture stent 100B as illustrated below in FIG. 8. Stent 100B is coupled to inner member 602, e.g., with anchors or other structures, to secure stent 100B during recapture. See for example anchors 130 at distal end 102 of FIG. 1. Use of anchors is well known to those of skill in the art and so is not discussed in detail.

FIG. 8 is a modified partial cross-section view of stent delivery system 600 of FIG. 7, stent 100B having been recaptured from the partial deployment shown in FIG. 7. Referring now to FIGS. 7 and 8 together, to recapture stent 100B, sheath 604 is advanced by the physician in the direction of arrow 702 (FIG. 7). Generally, retraction means motion of sheath 604 in the proximal direction opposite of arrow 702 and advancement means motion of sheath 604 in the distal direction of arrow 702.

As sheath 604 is advanced, a distal end 704 of sheath 604 contacts and collapses the deployed segments of stent 100B. Further, as sheath 604 is advanced, stent 100B is effectively pulled into sheath 604. Thus, the deployed segments of stent 100B are pulled straight as they are pulled into sheath 604. Specifically, the unconnected crowns are pulled straight. As the deployed segments are pulled straight and into sheath 604, stent 100B has an absence of loose ends or other protrusions that can catch on distal end 704 of sheath 604. Accordingly, stent 100B is readily recaptured within sheath 604. Further, by pulling the proximal end of the stent back into the outer sheath, as with anchors well-known by someone skilled in the art, as the unconnected crowns catch on the outer sheath they are forced to straighten, thus allowing them to fit within the sheath as shown in FIG. 7. Accordingly, the stent is recapturable.

Sheath 604 is advanced until stent 100B is entirely covered by sheath 604. Once stent 100B is covered by sheath 604, stent 100B is repositioned as shown in FIG. 8. Sheath 604 is then again retracted thus re-deploying stent 100B as shown in FIG. 9.

This disclosure provides exemplary embodiments according to the present invention. The scope of the present invention is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A method comprising:
   stretching a self-expanding stent along a longitudinal axis of said self-expanding stent by pulling an end of said self-expanding stent along said longitudinal axis, wherein prior to said stretching, said self-expanding stent comprises:

a plurality of segments having an alternating repeating pattern;

each of said segments having connected crowns and unconnected crowns, wherein each cell of said self-expanding stent comprises two opposing unconnected crowns between adjacent connected crowns, said unconnected crowns comprising smooth curves;

connectors extending between and connecting adjacent connected crowns of adjacent segments;

said stretching comprising straightening said unconnected crowns such that said segments include straight sections between said adjacent connected crowns, said method further comprising allowing said unconnected crowns to return to said smooth curves such that said plurality of segments return to said alternating repeating pattern subsequent to said stretching.

2. The method of claim 1 wherein said straightening said unconnected crowns comprises causing said unconnected crowns to extend into a straight position.

3. The method of claim 1 wherein said unconnected crowns are straightened without damage or permanent distortion to said unconnected crowns.

4. The method of claim 1 wherein said stretching is performed until said self-expanding stent is nearly fully stretched along said longitudinal axis.

5. The method of claim 1 wherein said straight sections are approximately parallel to said longitudinal axis.

6. The method as claim 1 wherein each of said straight sections when relaxed comprises at least one straightened unconnected crowns.

7. The method of claim 1 wherein each of said straight sections when relaxed comprises two straightened unconnected crowns.

8. A method comprising:

inserting a stent delivery system into a vessel, said stent delivery system comprising:

a nearly fully stretched self-expanding stent comprising:

a plurality of segments;

each of said segments comprising connected crowns and straight sections extending between adjacent ones of said connected crowns, said straight sections when relaxed comprising unconnected crowns that have been straightened;

connectors extending between and connecting adjacent connected crowns of adjacent segments;

wherein prior to said self-expanding stent being nearly fully stretched by pulling an end of said self-expanding stent along said longitudinal axis, said self-expanding stent comprises:

said plurality of segments having an alternating repeating pattern;

each of said segments having said connected crowns and said unconnected crowns, wherein each cell of said self-expanding stent comprises two opposing unconnected crowns between adjacent connected crowns, said unconnected crowns comprising smooth curves;

a sheath radially constraining said nearly fully stretched self-expanding stent; and retracting said sheath to expose at least a first segment of said stent, said first segment of said stent self-curling and radially self-expanding to return to said alternating repeating pattern.

9. The method of claim 8 wherein said self-curling comprises returning said unconnected crowns to a smooth curve relaxed configuration.

10. The method of claim 9 wherein said returning said unconnected crowns to a smooth curve relaxed configuration comprises returning said straight sections to a curved relaxed configuration.

11. The method of claim 8 further comprising advancing said sheath to recapture said stent.

12. The method of claim 11 wherein said advancing said sheath comprises pulling said stent straight and into said sheath.

13. The method of claim 12 wherein said stent has an absence of loose ends or other protrusions that can catch on a distal end of said sheath.

14. The method of claim 12 wherein said pulling said stent straight comprises straightening said unconnected crowns.

* * * * *